(12) United States Patent
Evensson

(10) Patent No.: US 8,397,726 B2
(45) Date of Patent: Mar. 19, 2013

(54) SMALL SIZE BREATHING PROTECTIVE DEVICE ARRANGED TO BE HELD IN THE USERS MOUTH

(75) Inventor: Anders Evensson, Molkom (SE)

(73) Assignee: Filtoro Aktiebolag (SE)

( * ) Notice: Subject to any disclaimer, the term of this patent is extended or adjusted under 35 U.S.C. 154(b) by 861 days.

(21) Appl. No.: 12/515,575

(22) PCT Filed: Nov. 19, 2007

(86) PCT No.: PCT/SE2007/050868
§ 371 (c)(1),
(2), (4) Date: May 20, 2009

(87) PCT Pub. No.: WO2008/063126
PCT Pub. Date: May 29, 2008

(65) Prior Publication Data
US 2010/0059060 A1   Mar. 11, 2010

Related U.S. Application Data

(60) Provisional application No. 60/866,438, filed on Nov. 20, 2006.

(51) Int. Cl.
*A62B 7/10* (2006.01)
(52) U.S. Cl. .............................. 128/205.29; 128/206.29
(58) Field of Classification Search ............. 128/201.13, 128/201.25, 201.26, 205.12, 205.27, 205.29, 128/206.15–206.17, 206.29
See application file for complete search history.

(56) References Cited

U.S. PATENT DOCUMENTS

| | | | | |
|---|---|---|---|---|
| 657,866 A | * | 9/1900 | Fike ........................ | 128/204.13 |
| 1,043,689 A | * | 11/1912 | Gottlieb ................... | 128/204.13 |
| 3,658,058 A | | 4/1972 | Neidhart et al. | |
| 3,669,109 A | * | 6/1972 | Cheffers et al. .......... | 128/204.17 |
| 3,747,598 A | * | 7/1973 | Cowans .................... | 128/201.13 |
| 5,320,096 A | * | 6/1994 | Hans ......................... | 128/205.29 |
| 5,771,885 A | | 6/1998 | Putrello | |
| 5,957,131 A | | 9/1999 | Hutchinson et al. | |

(Continued)

FOREIGN PATENT DOCUMENTS

EP   0695561 A1   2/1996
WO   92/21408 A1   12/1992

(Continued)

OTHER PUBLICATIONS

International Search Report for PCT/SE2007/050868.

(Continued)

*Primary Examiner* — Loan Thanh
*Assistant Examiner* — Kathryn E Ditmer
(74) *Attorney, Agent, or Firm* — Brooks Kushman P.C.

(57) ABSTRACT

A breathing protective device comprising a tubular elongated filter housing defining at least one wall between a first end and a second end, said wall having at least one opening, a filter in the filter house and a mouthpiece having an air canal with an opening arranged to be introduced into and held in the user's mouth whereby said filter house extends parallel to a line between the corners of the user's mouth, said air canal being in communication with at least one space within said housing for filtered inhalation air and exhalation air respectively, and wherein either the filter or the filter with the housing is disposable, wherein said filter is arranged to separate a first space from a second space and in that said air canal is arranged to enable supply of inhalation air from said first space via said filter and to enable exhalation air to escape via said opening from said second space.

11 Claims, 3 Drawing Sheets

U.S. PATENT DOCUMENTS

| | | | |
|---|---|---|---|
| 6,346,130 B2 * | 2/2002 | Suzuki | 55/311 |
| 6,401,860 B1 * | 6/2002 | Ellington et al. | 181/242 |
| 6,968,841 B2 * | 11/2005 | Fini | 128/204.17 |
| 6,986,348 B2 * | 1/2006 | Carter | 128/201.25 |

FOREIGN PATENT DOCUMENTS

| | | |
|---|---|---|
| WO | 9611037 A1 | 4/1996 |
| WO | 2004/041364 A1 | 5/2004 |
| WO | 2005000412 A1 | 1/2005 |
| WO | 2005/105216 A1 | 11/2005 |
| WO | 2007/042765 A1 | 4/2007 |

OTHER PUBLICATIONS

Supplemental European Search Report for EP07835451.
International Search Report for PCT/SE2007/050868.

* cited by examiner

SMALL SIZE BREATHING PROTECTIVE DEVICE ARRANGED TO BE HELD IN THE USERS MOUTH

CROSS-REFERENCE TO RELATED APPLICATION

This application claims the benefit of U.S. provisional application Ser. No. 60/866,438 filed Nov. 20, 2006.

TECHNICAL FIELD

This invention relates to a breathing protective device comprising a tubular elongated filter housing defining at least one wall between a first end and a second end, said wall having at least one opening, a filter in the filter house and a mouthpiece having an air canal with an opening arranged to be introduced into and held in the user's mouth whereby said filter house extends parallel to a line between the corners of the user's mouth, said air canal being in communication with at least one space within said housing for filtered inhalation air and exhalation air respectively, and wherein either the filter or the filter with the housing is disposable.

BACKGROUND OF THE INVENTION

Breathing protective devices used today are either very advanced, e.g. conventional gas masks, or more simple breathing protective devices that cover the mouth and nose. Gas masks have their given field of use in extremely dangerous environments that require advanced air purification. Simple, conventional breathing protective devices that cover the mouth and nose are widely used for lack of anything else, in environments also requiring air purification, despite such devices being uncomfortable and in many cases having insufficient purification ability and other drawbacks.

Breathing protective devices of a kind having a mouthpiece arranged to be introduced into and held in the user's mouth have also been suggested. As examples of such breathing protective devices reference can be made to those described in WO 05/105216, WO 92/21408, EP 0 695 561 A1, U.S. Pat. No. 5,771,885, U.S. Pat. No. 5,957,131 and DE-OS 2 115 715. However, all protective devices shown in these publications have some or several deficiencies and/or drawbacks and have as far as the applicant is aware not come to any wide use.

BRIEF ACCOUNT OF THE INVENTION

Given the above background, the invention aims at providing a breathing protective device of the type mentioned in the introduction above, will provide for a perfectly satisfactory protection in many work environments and that has many practical advantages in addition. More specifically, the invention aims at providing a breathing protective device that fulfils most of the following advantages and/or requirements:

A good purifying effect
A small breathing resistance both at inhalation and at exhalation
A small size (pocket-size)
A low weight
No interference with the users visual field; not having any far projecting parts
Can be used by persons having a moustache or beard
Can be rationally produced
The filter is easy to insert and remove for exchange or cleaning
A large degree of utilization of space available for air purification
Can be used with different filter grades adapted to the requirements of the environment of use All, or at least most of the qualities mentioned above can be attained by a breathing protective device of the type mentioned in the introduction, characterised in that:

said filter is arranged to separate a first space from a second space,
said air canal is arranged to enable supply of inhalation air from said first space via said filter, and
to enable exhalation air to escape via said opening from said second space.

Thanks to the invention a very cost efficient design is achieved that provides many advantages. One important advantage is that there is a need for only one check valve to achieve the needed function of the breathing protecting device and according to a preferred embodiment the support structure of said check valve may be integrated of the filter housing. Another important advantage that the filter in itself is used to separate the space for incoming inhalation air from the space for exhalation air, without any need of using costly extra barriers or walls, but the existing resistance of the filter in itself is used to achieve the separation of said spaces. Accordingly the exhalation air will not pass through the filter, which is an important advantage in many applications.

According to further aspects of the invention:

that said second space circumferentially surrounds said first space, preferably in a substantially coaxial manner, which improves the ability of creating a compact breathing protection device having high filtering capacity.
that said filter is curved in a plane that is perpendicular to the longitudinal direction of the filter house, and preferably that said filter is arranged with a plurality of folds in the longitudinal direction of the filter house to form a folded, star shaped body in a perpendicular cross-section, which further increases the ability of creating a compact breathing protection device having a high filtering capacity.
that the whole breathing protecting device is disposable, which provides the advantage that exhalation air that is expelled through the opening has traveled substantial equal distances independent if passing through the upper portion or the lower portion of said outer space and also providing an outlet of the exhalation air that may not disturb the user.

Additional characteristics and aspects of the invention are apparent from the claims and from the following detailed description of the invention.

BRIEF DESCRIPTION OF THE DRAWINGS

In the detailed description of the invention, reference will be made to the enclosed drawings, of which.

DETAILED DESCRIPTION OF THE INVENTION

Figure 1:
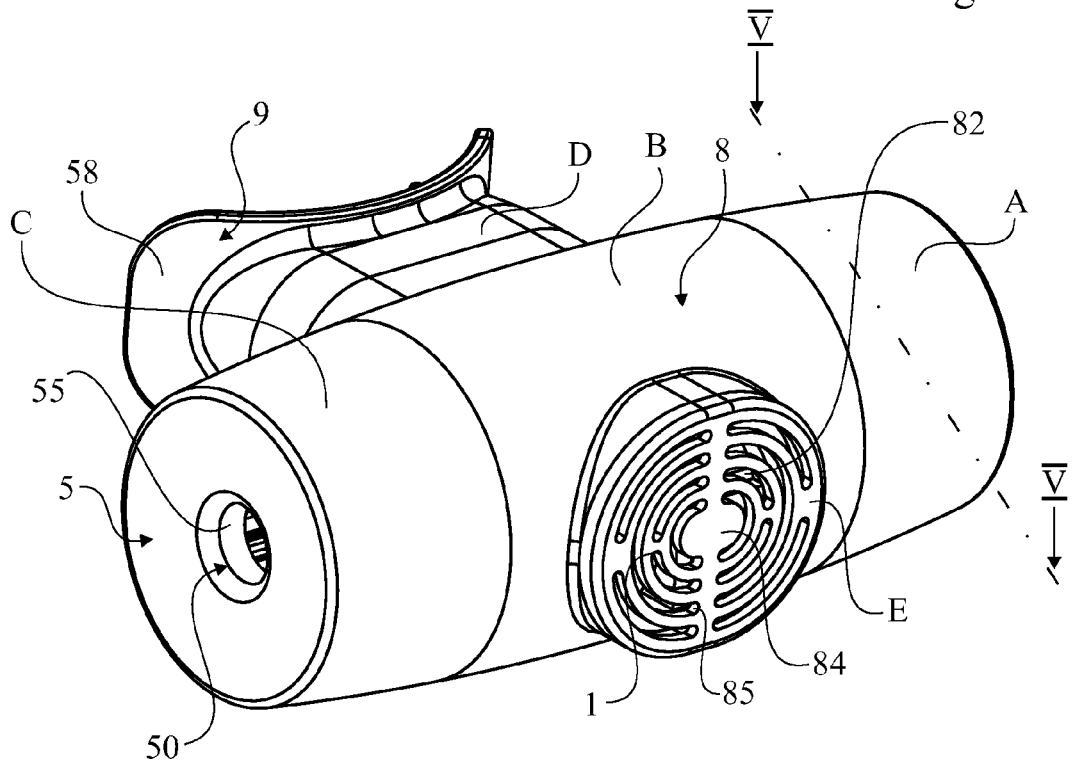
FIG. 1 shows a perspective view, obliquely from above, of breathing protective device according to the invention.
Figure 2:
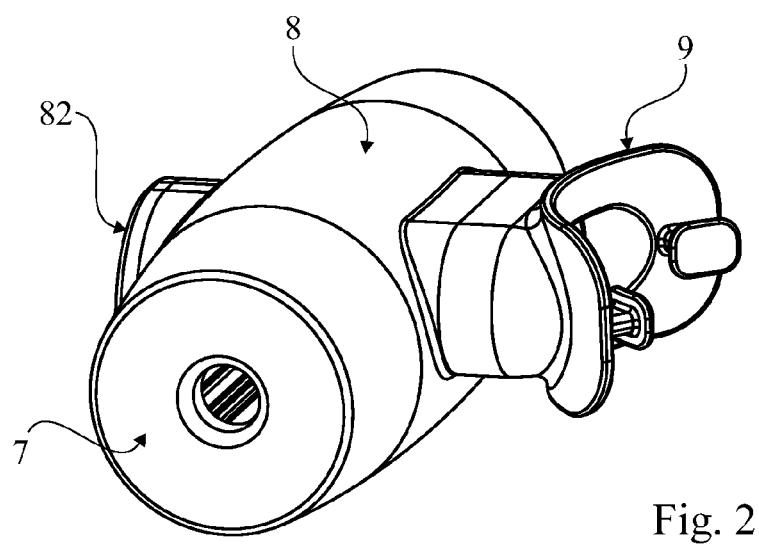
FIG. 2 shows another perspective view of the breathing protective device shown in FIG. 1, but seen from an opposite side.

According to FIGS. 1-5 a preferred embodiment of the invention is presented, which breathing protective device includes a filter housing 8, a filter 2 positioned within the filter housing 8, two openings 50, 70 for inhalation air, an opening 82 for exhalation air and a mouth piece 9.

The filter housing 8 is shaped as an elongated, substantially cylindrical tube that extends between a first end portion 5 and a second end portion 7. The filter housing 8, preferably has a total length of about 100 mm (+/−25%), and an outer diameter of about 30 mm (+/−25%) and a wall thickness of approximately 1-5 mm. At each end portion 5, 7 of the filter housing 8 there is an opening 50, 70, that leads into an inner central space 80. Each opening is provided with an inwardly extending annular portion 55, 75 arranged to engage/position the filter 2.

The mouth piece 9 is formed generally as is known per se from for example diving gears, comprising a tubular section 52, that forms a canal 51, having a front end leading into said housing 8 and a rear end debouching into an elongated opening 54, to be held in the mouth of a user. Adjacent the opening 54 there is arranged a pair of wings 58, that extend obliquely backwards and outwards, to provide dental fixing means 59.

The front end of canal 51 leads to a peripheral space 83 that is provided directly at the inside of the housing 8, which space 83 surrounds the filter 2 and is in direct communication with the opening 82 for exhalation air. To merely allow passage of exhalation air said opening 82 is provided with a check valve 1. This check valve 1 has the function to prevent air to enter into the space 83 when a person is inhaling through the mouth piece 9. Many different kind of known check valves may be used to achieve this function. In the shown embodiment there is used a check valve 1 comprising a number of moveable, flexible members 30 (membranes) that are overlapping, such that they may cover and seal the openings provided them between when there is a lower pressure within the space 83 than outside of the check valve 1. Hence this check valve 1 will open to let exhalation air out of the device, i.e. air coming via the canal 51 of mouth piece 9 and the space 83. The other way around the check valve 1 will be closed to allow air to enter via the inlets 50, 70, into the inner space 80, from the inner space 80 via the filter 2 into the outer peripheral space 83 and thereafter via canal 51 into the user, when the user of the breathing protective device inhales air, through the mouth piece 9.

Figure 3:
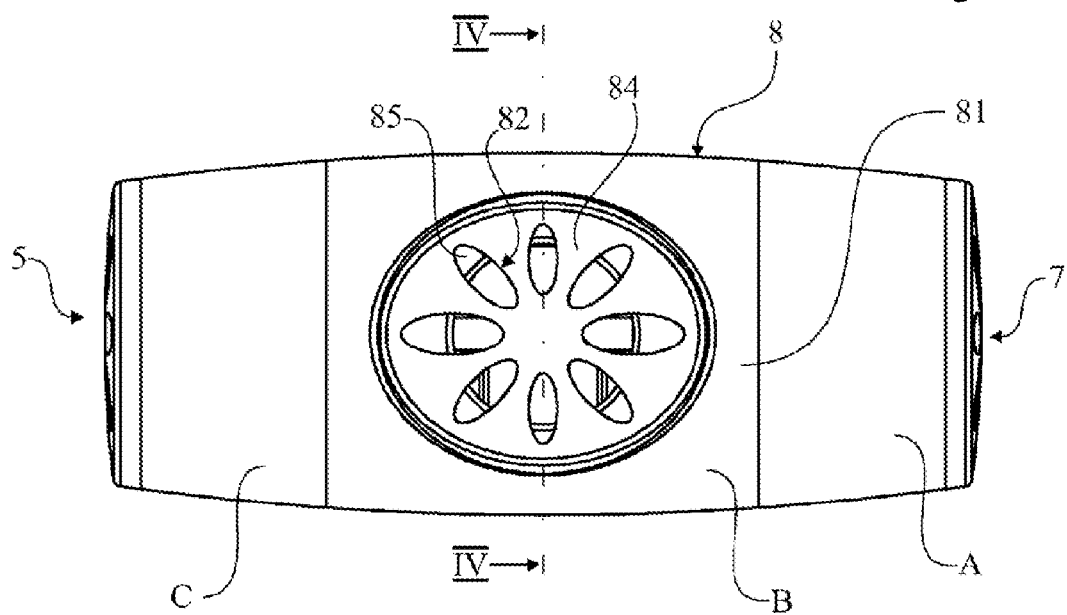
FIG. 3 shows a front view of the breathing protective device shown in FIGS. 1 and 2, but presenting a modification regarding protective caps.
Figure 4:
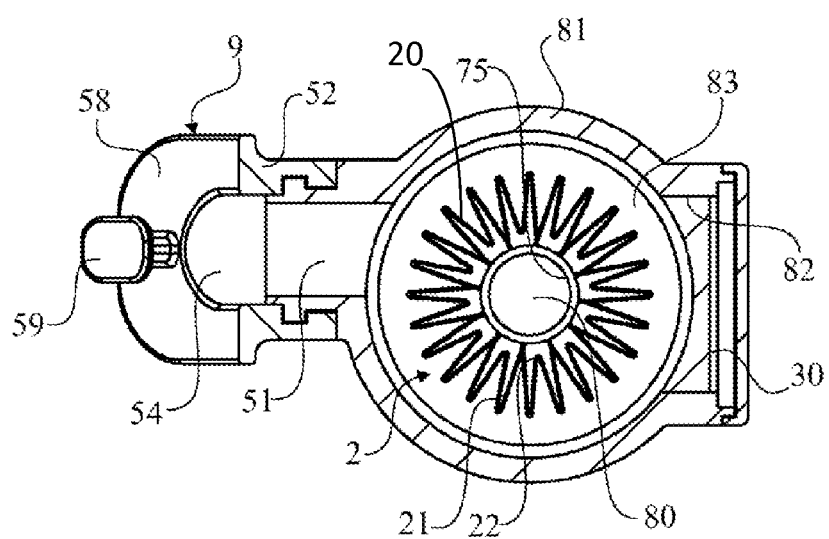
FIG. 4 shows a cross-sectional vertical view of along IV-IV as marked in FIG. 3.
Figure 5:
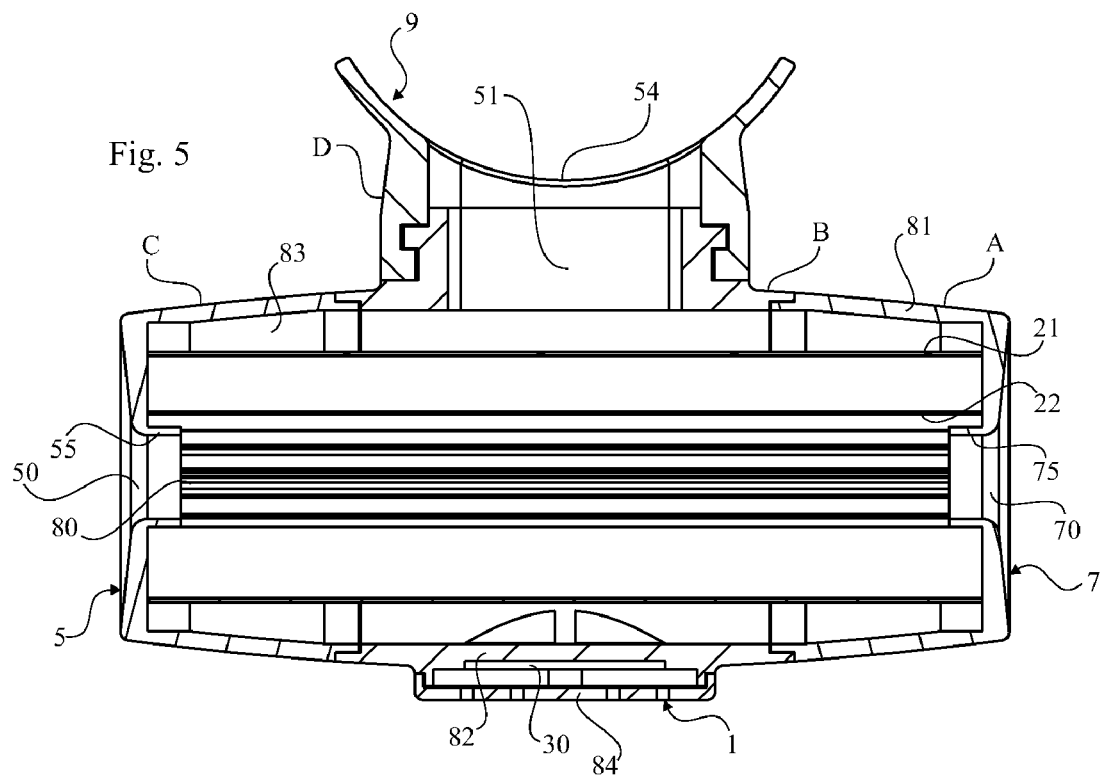
FIG. 5 shows a cross-sectional view along V-V as marked in FIG. 1.

Further it is shown (see FIG. 1) that the front opening 82 is provided with a protection cap 84 arranged with a plurality of openings 85 (here in the form of curved grooves), presenting a sufficient total area of openings to allow for an appropriate flow of air without undue resistance and also protecting the filter by not allowing larger objects to pass through the cap 84. In FIG. 3 it is shown that the form of the openings 85 may vary, e.g. to extend radially, which in many applications may present an advantage. Further FIG. 3 shows that protective caps 84, may also be used to protect each one of, or at least one of, the openings 50, 70 at the ends 5, 7. In one embodiment all caps 84 may have the same design/size, which provides scale advantages.

The filter 2 is supported by the annular portions 55, 75 at each end 5, 7 of the filter housing 8. Hence the filter 2 has an inner diameter that fits onto said annular portions 51, 71, and a sufficient length to allow these portions 55, 75 to protrude into the central space of the filter 2, to securely fix the filter 2 in the housing. The filter 2 is preferably of a folded type, presenting a cross-sectional star shape, i.e. made of a filter web 20 that is provided with a plurality of inner folds 22 and outer folds 21 and that has been joined to form a circular arc of 360°.

The preferred breathing protective device has such a shape and according to the preferred embodiment also such dimensions that it can be kept in a small bag, that can be attached for example to a belt, or even in a pocket in the work clothes of the user.

When the breathing protective device 1 is to be used, the mouth piece 9 is inserted into the users mouth, while the nostrils may be sealed in a conventional way, for example by a noose clip that can be attached to the breathing protective device (not shown). When the user inhales the non-return valve 1 seals to allow air to pass into the inner space 80. Accordingly air is sucked in via the openings 50, 70, into the inner space 80 of the filter house 8, via the filter 2 into the outer space 83, thereafter through the canal 51 within the mouth piece 9 out through the opening 54 into the mouth of the user. The breathing resistant caused by the breathing filter 2, is small, especially in relation to the small dimensions of the breathing protective device. This is due to the filter 2 having a comparatively large surface, thanks to its length and its folded design. The arc-like distribution over the filter surface, of the air that is sucked in, also promotes a low breathing resistant. At exhalation, the breathing resistance of the breathing protective device is almost negligible. The canal 51 and tubular outer space 82 are wide, and the membranes 30 open up at extremely low overpressure, thereby providing a device with hardly any noticeable resistance. Thanks to this design, and the fact that the filter 2 does provide some resistance no (or at least very small amounts) of exhalation air will pass through the filter 2, which is an important advantage since normally this kind of filter material is negatively influenced by humidity.

The breathing protective device, shown in FIG. 1-5 is formed of five parts A-E, to allow for cost efficient production by means of form moulding in plastics. As can be seen a mouth piece 9 may be provided that is intended for multiple use, i.e. merely the filter house 8, containing the filter 2, may be made disposable or indeed merely the filter 2.

A type of filter having the trade name Technostat, 200 $gr/m^2$ is suitable when the breathing protective device according to the invention is to be used e.g. in dusty construction sites or by persons having allergy troubles for e.g. canine, feline or bovine hair or pollen. In environments containing cement powder, stone and/or carbon dust, a filter stuff should be used that is finer than the one in Technostat, 200 $gr/m^2$, in which case the filter however may have the same design as the described one and be manufactured by the company mentioned above or some other manufacturer. In principle, still finer filter stuffs can be used in the filter that is part of the breathing protective device according to the invention, e.g. filter stuffs containing activated carbon, ion-exchanger materials or other absorbents or adsorbents for uptake of gaseous or vaporous pollutants, as well as welding fume and other fumes.

The invention is not delimited by what has been mentioned above in relation to the preferred embodiments, but may be vary within the scope of the appended claims. Accordingly, the filter house 8 e.g. may be of varying shapes, e.g. a tube with an orthogonal cross-section. Moreover, the term wall 81 evidently must be given a very broad definition, since also in embodiments having a minor part of the circumference covered by a wall or mesh-portion, there is created a design defining a wall-like imaginary structure. Furthermore it is evident that the openings 50, 70 for passage of air into the space 80 within the filter house 8 can be given varying shapes and sizes than shown above, without impairing the functional the breathing protective device in any way, given that the total area of that opening is kept within optimal ranges. In this connection it is evident for the skilled person that this may also be achieved by the use of merely one opening 50. Is should also be mention that the filter 2 can be of another type than described above.

The invention claimed is:

1. A breathing protective device comprising: a tubular elongated filter housing defining at least one wall between a first end and a second end, said wall having at least one opening, a filter in the filter house and a mouthpiece having an air canal with an opening arranged to be introduced into and held in the user's mouth whereby said filter house extends parallel to a line between the corners of the user's mouth, said air canal being in communication with at least one space within said housing which is configured to receive filtered inhalation air and exhalation air during inhalation and exhalation, respectively, and wherein either the filter or the filter with the housing is disposable, wherein said filter is arranged to coaxially separate a first space from a second space, the second space coaxially surrounding the first space, and in that said air canal is arranged to enable supply of inhalation air from said first space via said filter and to enable exhalation air to escape via said opening in said wall from said second space.

2. A breathing protective device according to claim 1, wherein said opening in said wall is arranged with a check valve.

3. A breathing protective device according to claim 1, wherein said filter is curved in a plane that is perpendicular to the longitudinal direction of the filter house.

4. A breathing protective device according to claim 3, wherein said filter is arranged with a plurality of folds in the longitudinal direction of the filter house to form a folded, star shaped body in a perpendicular cross-section.

5. A breathing protective device according to claim 4, wherein a long-axis of the filter is arranged essentially straight in the longitudinal direction of the filter house.

6. A breathing protective device according to claim 4, wherein at least the outer surface of the filter is arranged with a curvature having a radius of between 5 mm-20 mm.

7. A breathing protective device according to claim 1, wherein the whole breathing protecting device is disposable.

8. A breathing protective device according to claim 1, wherein said opening in said wall, in relation to said canal, is positioned at least substantially opposite in said housing.

9. A breathing protective device according to claim 1, wherein the filter extends 360 degrees around a longitudinal axis of the filter housing to form a circular arc.

10. A breathing protective device according to claim 1, wherein said first and second end have a substantially circular configuration.

11. A breathing protective device according to claim 1, wherein the filter is in the form of a continuous web arranged to define said first space in its center, and being supported at its ends by annular portions protruding inwardly from each end of the housing.

\* \* \* \* \*